US012641050B1

(12) United States Patent
Shaft

(10) Patent No.: US 12,641,050 B1
(45) Date of Patent: May 26, 2026

(54) SYSTEM AND METHODS FOR UNIVERSAL SECURE MESSAGING

(71) Applicant: Dignity Health, San Francisco, CA (US)

(72) Inventor: Judd Daniel Shaft, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 18/745,829

(22) Filed: Jun. 17, 2024

Related U.S. Application Data

(60) Provisional application No. 63/508,484, filed on Jun. 15, 2023.

(51) Int. Cl.
*G06F 15/16* (2006.01)
*G16H 80/00* (2018.01)
*H04L 51/56* (2022.01)

(52) U.S. Cl.
CPC ............. *H04L 51/56* (2022.05); *G16H 80/00* (2018.01)

(58) Field of Classification Search
CPC ................................ H04L 51/56; G16H 80/00
USPC ......................................................... 709/206
See application file for complete search history.

(56) References Cited

U.S. PATENT DOCUMENTS

| | | | | |
|---|---|---|---|---|
| 6,990,514 B1 * | 1/2006 | Dodrill | ................... | G06F 16/84 709/219 |
| 7,275,215 B2 * | 9/2007 | Werndorfer | ............. | G06F 3/167 715/752 |
| 7,308,477 B1 * | 12/2007 | Gress | .................. | H04L 63/0428 379/279 |
| 7,366,795 B2 * | 4/2008 | O'Neil | .................. | H04W 4/029 709/219 |
| 7,631,266 B2 * | 12/2009 | Werndorfer | ............. | H04L 51/04 715/752 |
| 7,707,047 B2 * | 4/2010 | Hasan | .................... | G16H 70/60 705/2 |
| 7,716,289 B2 * | 5/2010 | Malik | .................... | H04L 51/04 709/204 |
| 7,921,369 B2 * | 4/2011 | Bill | .......................... | H04L 51/04 715/810 |
| 7,941,165 B2 * | 5/2011 | Wright | .................... | H04W 4/14 709/206 |
| 8,037,150 B2 * | 10/2011 | Weaver | .................. | H04L 51/04 455/518 |
| 8,095,603 B2 * | 1/2012 | Hung | ..................... | H04L 67/56 709/202 |
| 8,112,487 B2 * | 2/2012 | Leedberg | .............. | H04L 51/212 709/204 |
| 8,135,787 B2 * | 3/2012 | Bansal | .................... | H04L 51/04 709/204 |
| 8,145,714 B2 * | 3/2012 | Barry | .................... | G06Q 30/02 709/206 |
| 8,306,228 B2 * | 11/2012 | Le Saint | ............. | H04L 63/0421 380/278 |
| 8,595,295 B2 * | 11/2013 | Wherry | ................. | H04L 67/306 709/204 |
| 8,631,078 B2 * | 1/2014 | Wherry | .................. | H04L 51/04 709/206 |

(Continued)

*Primary Examiner* — Alicia Baturay

(74) *Attorney, Agent, or Firm* — Polsinelli PC

(57) ABSTRACT

Various embodiments of a computer-implemented system for universal secure messaging in a clinical setting including a messaging broker are disclosed.

15 Claims, 4 Drawing Sheets

(56) References Cited

U.S. PATENT DOCUMENTS

| | | | | |
|---|---|---|---|---|
| 8,650,253 | B2 * | 2/2014 | Smedley | A63F 13/12 |
| | | | | 709/204 |
| 8,930,460 | B2 * | 1/2015 | Wherry | G06F 16/95 |
| | | | | 709/204 |
| 8,965,964 | B1 * | 2/2015 | Odell | H04L 51/046 |
| | | | | 709/219 |
| 8,995,769 | B2 * | 3/2015 | Carr | G06V 30/224 |
| | | | | 709/206 |
| 9,002,949 | B2 * | 4/2015 | Appleman | H04L 51/04 |
| | | | | 709/206 |
| 9,015,155 | B2 * | 4/2015 | Levinson | H04L 51/04 |
| | | | | 707/728 |
| 9,059,840 | B2 * | 6/2015 | Connelly | H04L 9/14 |
| 9,608,945 | B2 * | 3/2017 | Thirumalai | H04L 12/1859 |
| 9,716,619 | B2 * | 7/2017 | Bellan | H04L 65/1104 |
| 9,961,037 | B2 * | 5/2018 | Li | H04L 51/066 |
| 10,097,593 | B2 * | 10/2018 | Knezevic | H04W 36/22 |
| 10,454,762 | B2 * | 10/2019 | Bellan | H04L 65/60 |
| 10,460,290 | B2 * | 10/2019 | Levinson | G06Q 10/107 |
| 10,680,994 | B2 * | 6/2020 | Li | H04L 51/52 |
| 11,075,875 | B2 * | 7/2021 | Li | H04L 51/066 |
| 11,171,980 | B2 * | 11/2021 | Coffey | H04L 63/1425 |
| 11,671,798 | B2 * | 6/2023 | Brooks | H04W 4/14 |
| | | | | 455/412.2 |
| 11,700,216 | B2 * | 7/2023 | Brooks | H04L 63/08 |
| | | | | 709/206 |
| 11,765,120 | B2 * | 9/2023 | Motamedi | H04L 67/55 |
| | | | | 709/206 |
| 11,785,429 | B2 * | 10/2023 | Rubin | G06Q 50/01 |
| | | | | 455/466 |
| 12,033,732 | B2 * | 7/2024 | Speirs | G16H 40/67 |
| 2001/0003202 | A1 * | 6/2001 | Mache | H04W 12/06 |
| | | | | 713/153 |
| 2004/0218762 | A1 * | 11/2004 | Le Saint | H04L 9/0825 |
| | | | | 380/277 |
| 2006/0085515 | A1 * | 4/2006 | Kurtz | H04L 51/04 |
| | | | | 709/207 |
| 2009/0112623 | A1 * | 4/2009 | Schoenberg | G06Q 10/02 |
| | | | | 705/2 |
| 2010/0169417 | A1 * | 7/2010 | Rukman | H04W 4/12 |
| | | | | 709/206 |
| 2010/0216495 | A1 * | 8/2010 | Kristiansson | H04L 51/04 |
| | | | | 455/466 |
| 2010/0222085 | A1 * | 9/2010 | El Bedraoui | H04L 51/58 |
| | | | | 455/466 |
| 2010/0318620 | A1 * | 12/2010 | Bansal | H04L 51/216 |
| | | | | 709/206 |
| 2011/0010197 | A1 * | 1/2011 | Schoenberg | G06Q 10/10 |
| | | | | 715/708 |
| 2011/0249621 | A1 * | 10/2011 | Harris | H04M 7/003 |
| | | | | 370/328 |
| 2013/0073636 | A1 * | 3/2013 | Zhu | H04L 12/1818 |
| | | | | 709/206 |
| 2014/0040404 | A1 * | 2/2014 | Pujare | H04L 51/04 |
| | | | | 709/206 |
| 2014/0214450 | A1 * | 7/2014 | Bechtold | G06Q 10/10 |
| | | | | 705/3 |
| 2015/0127358 | A1 * | 5/2015 | Porter | G16H 40/20 |
| | | | | 705/2 |
| 2015/0381571 | A1 * | 12/2015 | Plasse | G16H 40/67 |
| | | | | 726/26 |
| 2016/0006683 | A1 * | 1/2016 | Pujare | H04L 65/1104 |
| | | | | 709/206 |
| 2016/0036760 | A1 * | 2/2016 | van Gent | H04L 51/046 |
| | | | | 709/206 |
| 2016/0071171 | A1 * | 3/2016 | Cancelliere, III | |
| | | | | G06Q 10/06398 |
| | | | | 705/2 |
| 2024/0388562 | A1 * | 11/2024 | Yao | H04L 67/02 |

* cited by examiner

SYSTEM AND METHODS FOR UNIVERSAL SECURE MESSAGING

CROSS-REFERENCE TO RELATED APPLICATIONS

This is a Non-Provisional application that claims benefit to U.S. Provisional Application Serial No. 63/508,484, filed on Jun. 15, 2023, which is herein incorporated by reference in its entirety.

FIELD

The present disclosure generally relates to messaging platforms; and in particular, to systems and methods for secure universal communication between users suitable for a medical or health care environment.

BACKGROUND

In healthcare, there are a number of secure messaging/ physician on-call management systems available for pur- chase/subscription (e.g. American Well (Dignity's One- Pass), BeckonCall, TigerConnect, Imprivata, and DataMotion). Each of these system functions as a secure messaging and/or physician on-call management solution, and are typically suitable for individual healthcare physician practices. However, from a hospital-based facility perspec- tive, these conventional technologies lack universal integra- tion.

For example, inpatient nurses in a hospital are often required to use a specific HIPAA compliant messaging application to connect with external providers re: patient care (e.g. OnePass). However, most of the external providers are unwilling to use the hospital's system, as they are comfortable with, and have subscribed to, their own secure messaging/on-call management solutions. The result, nurses or other medical workers may ultimately end up either using the provider's preferred secure app to communicate patient care information, though the provider's app has not been approved for this use by the hospital facility. In some cases, clinical staff may simply elect to text protected health information (PHI) protected health information via standard text messaging, as it is too complex to determine which application to use for which provider. This situation opens the nurse and hospital facility up to the risk of sharing PHI via unapproved means, including breaches of PHI. Though the inpatient facilities wish to mandate a single platform to use for the nurses and allied health staff, the external practices/providers are unwilling and otherwise face various technical challenges, as this would require maintenance in multiple applications, and the use of multiple secure texting apps to serve their clinical needs.

It is with these observations in mind, among others, that various aspects of the present disclosure were conceived and developed.

BRIEF DESCRIPTION OF THE DRAWINGS

Corresponding reference characters indicate correspond- ing elements among the view of the drawings. The headings used in the figures do not limit the scope of the claims.

DETAILED DESCRIPTION

Figure 1A:
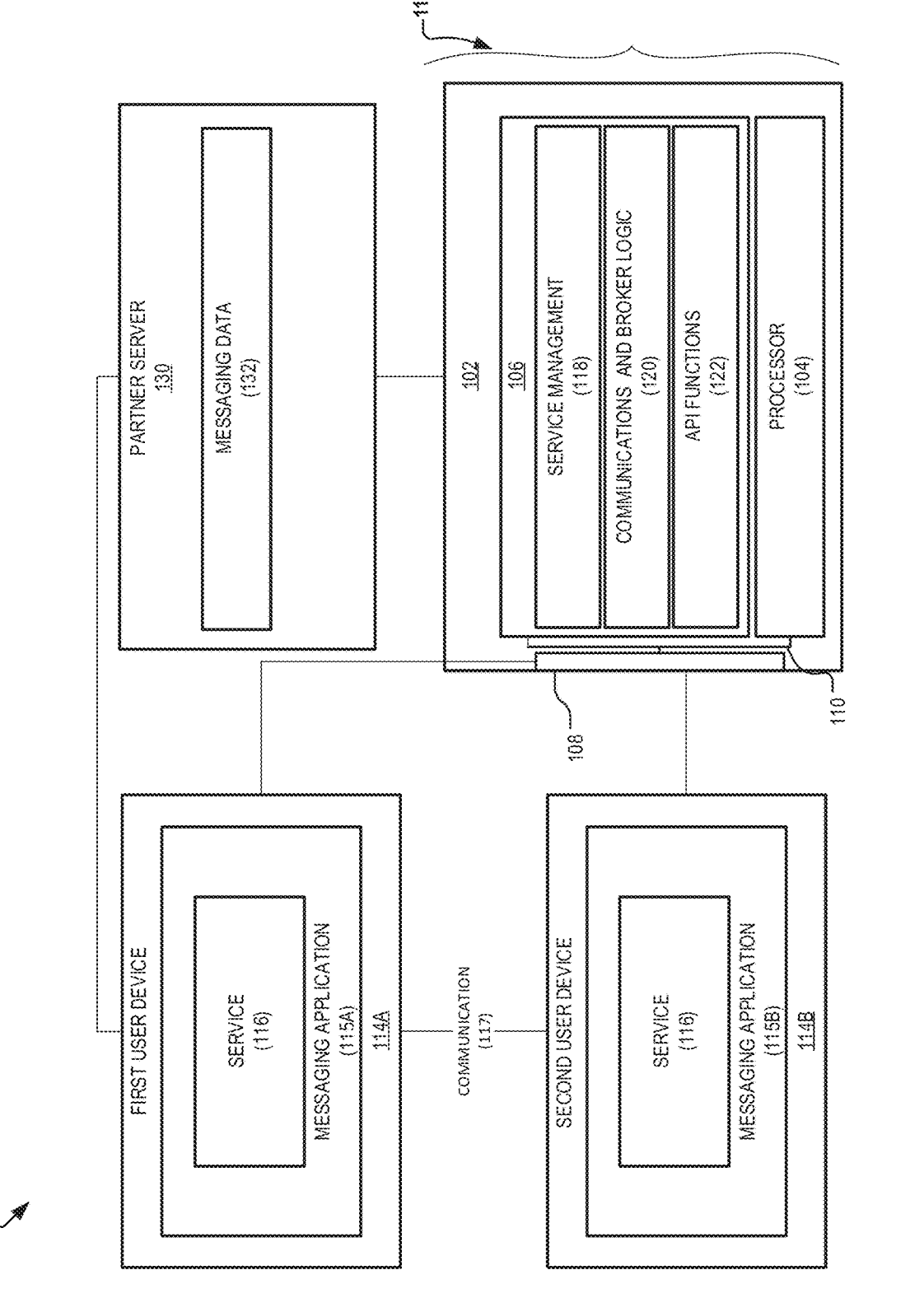
FIG. 1A is a simplified block diagram of a computer- implemented system for universal secure messaging.

Aspects of the present disclosure relate to embodiments of a computer-implemented universal secure messaging system ("system"). In some embodiments, the system includes a secure messaging broker, provided by a service imple- mented with communications between end-user devices or otherwise, that securely brokers communication between different messaging platforms. As such, the system accom- modates secure universal communications between hospital facility staff and patient care providers. In some embodi- ments, the system provides a single agnostic communication application, which can facilitate secure bi-directional com- munications with other secure message applications on the market.

Numerous advantages may be realized by the novel system disclosed herein. In some embodiments, the system includes a single application for hospital and clinic-based staff; any secure messaging tool used by external providers. With the system, hospitals will no longer need to convince private practice physicians that they must use the hospital's communication tool. The provider can now continue with their preferred system when communicating about patient care. On the other side, nursing staff, for example, no longer need to worry about which tool to use, download, etc. to communicate with varied providers. They access one appli- cation or service, search for the physician, and then com- municate.

In other words, the system may include or otherwise define a platform-agnostic, secure messaging application or service for hospital systems and/or private practices, which then leverages Application Program Interfaces (APIs) to integrate with known software vendors in the secure mes- saging and on-call space. With a solution like this, nurses from any healthcare facility, will be able to use a single application to communicate with physicians or other health- care colleagues regarding patient care activities. This appli- cation can serve as both a secure communications and on-call schedule viewer. The convenience of one single application for nursing and allied health staff, while allowing private physician practices to continuing using their own, preferred solutions, is a win-win proposal, and eliminates unnecessary and unwanted risk for healthcare organizations. The incentive for these secure messaging vendors to par- ticipate is simply put. Healthcare facilities are looking for one solution to meet these messaging needs, and they don't want to force physicians and private practices to change.

The system directly addresses the challenges of technical incompatibilities between different platforms and messaging services currently being used by different medical workers. In some embodiments, when implemented, for example, a medical worker need not download or otherwise train on a new application or service. The secure messaging broker of the system simply brokers communications between differ- ent platforms and services on the back end by leveraging APIs specific to each platform or service, as further described herein.

Referring to FIG. 1A, any of the aforementioned embodi- ments of a system described herein may take the form of a computer-implemented system, designated system 100, which may be utilized for universal secure messaging. In general, the system 100 comprises a computing device 102 including a processor 104, a memory 106 of the computing device 102 (or separately implemented), a network interface (or multiple network interfaces) 108, and a bus 110 (or wireless medium) for interconnecting the aforementioned components. The network interface 108 includes the mechanical, electrical, and signaling circuitry for communicating data over links (e.g., wires or wireless links) within a network (e.g., the Internet). The network interface 108 may be configured to transmit and/or receive data using a variety of different communication protocols, as will be understood by those skilled in the art.

In general, the computing device 102 may be part of a platform 111 defined by the system 100 where the processor 104 of the computing device 102 implements aspects of the platform 111 to broker communications between a first user device 114A and a second user device 114B. To illustrate, as demonstrated in FIG. 1A, the first user device 114A is executing a first messaging application 115A, and the second user device 114B is executing a second messaging application 115B (different from the first messaging application 115A). These messaging applications 115 may include any messaging applications or services used for communication between medical workers including, e.g., American Well, BeckonCall, TigerConect, Imprivata, and the like. As would be understood and appreciated, these exemplary communication applications or services are often incompatible with one another in some form.

In some embodiments, the system 100 leverages a service 116 implemented by the first user device 114A and the second user device 114B to transmit (one or more of) a communication 117 between the first user device 114A and the second user device 114B, despite any incompatibilities between the messaging applications 115 executed by the user devices 114. The service 116 may include, without limitation, a web service, a plug-in, add-in, add-on, app, software development kit (SDK), application programming interface, or some other software component that provides aspects of the platform 111 or adds functionality of the platform 111 to each of the messaging applications 115, as further described herein. Where the messaging applications 115 include different electronic health record (EHR) systems, service 116 may be integrated with each EHR system to accommodate communication between devices with such different EHR systems, regardless of a provider or other medical worker's choice of a system.

The platform 111 including possible services executed by the computing device 102 may include service management 118 for distributing and managing the distribution of the service 116 to end-user devices such as the user devices 114, communications and broker logic 120 for interpreting the content the communication 117 or data transmitted between the devices 114, and API functions 122 for accessing APIs associated with the first messaging application 115A and the second messaging application 115B, and brokering the communication 117 as further described herein. Any of the functionality provided by the computing device 102 and the platform 111 for authentication and providing the service 116, such as the functionality defined by the service management 118, the communications and broker logic 120, and/or the API functions 122, may be implemented as code and/or machine-executable instructions stored in the memory 106 and executable by the processor 104 that may represent one or more of a procedure, a function, a subprogram, a program, a routine, a subroutine, a module, an object, a software package, a class, or any combination of instructions, data structures, or program statements, and the like. In other words, one or more of functions of the platform 111 and/or computing device 102 described herein may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium (e.g., the memory 106), and the processor 104 performs the tasks defined by the code.

As further shown, the computing device 102 and/or the user devices 114 may be in operable communication, via the network interface 108, or otherwise, with a partner server 130 which has access to messaging data 132. As one example of how the partner server 130 is utilized with the system 100, the partner server 130 manages, supports, or is otherwise associated with the (first) messaging application 115A, and the first user device 114A receives or accesses the messaging application 115A from the partner server 130. The messaging data 132 available to the partner server 130 includes information (including protocols, data formats, fields, etc.) about how the messaging application 115A transmits data including communications between devices using the messaging application 115A. The computing device 102 accesses aspects of the messaging data 132, or otherwise communicates with the partner server 130 (via an API or otherwise) in order to process the communication 117 in some form to make it compatible between the devices 114, as further described herein. It should be understood that the components illustrated are non-limiting and exemplary, and additional components are contemplated.

Figure 1B:
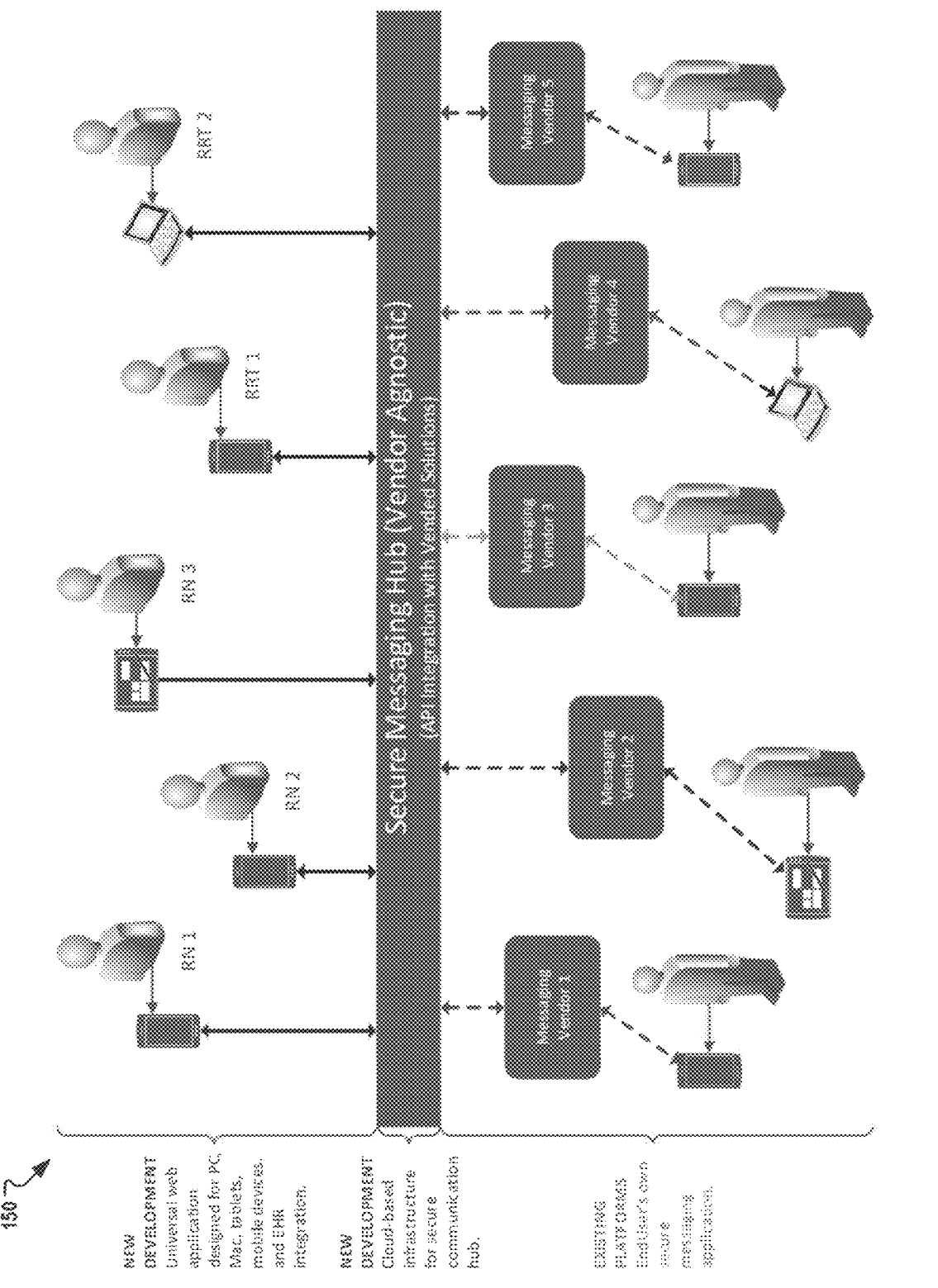
FIG. 1B is an image illustrating a secure messaging hub for universal secure messaging as described herein.

Referring to FIG. 1B, an exemplary secure messaging hub designated as hub 150 is shown for providing universal secure messaging. The hub 150 effectively functions as a secure messaging broker, and may be provided by implementation of the service 116 or otherwise provided. As indicated, the hub 150 as formed can provide bi-directional API communications, and provides a single interface or "umbrella" solution for clinical/medical workers. As further indicated, the hub 150 (and the computing device 102) may be implemented using cloud-based infrastructure to provide scalability of the hub 150 and other advantages. The hub 150 may incorporate any aspects of the system 100 or functionality of FIG. 2 described herein. In some embodiments, the hub 150 accommodates the following steps for facilitating a communication between a medical worker and a physician despite each of the medical worker and the physician utilizing a different messaging application or platform:

Medical worker finds a physician

Medical worker utilizes a user device to send a message or contact on-call resource via calendar feature (of a messaging application such as messaging application 114A) to the user device of a physician Universal Secure Communication hub 150 facilitates communication and brokers messaging between the messaging system used by the medical provider and the messaging system used by the physician Physician can communicate back to medical worker via their own secure messaging system Medical worker receives secure messaging back via the "Umbrella" solution of the hub 150.

The illustrated hub 150 of FIG. 1B shows a plurality of medical workers engaging the hub 150 in some capacity for universal messaging. In the example shown, the medical workers include registered nurses (RNs) and rapid response teams (RRTs). As indicated, existing platforms can plug-in or otherwise be integrated into the hub 150 via API integration or otherwise. In some embodiments, the hub 150 is comprised of cloud-based infrastructure for secure universal communications. In some embodiments, the hub 105 comprises a universal web application that can integrate a variety of end user devices such as personal computers (PCs), laptops, mobile devices, and the like for EHR integration.

Figure 2:
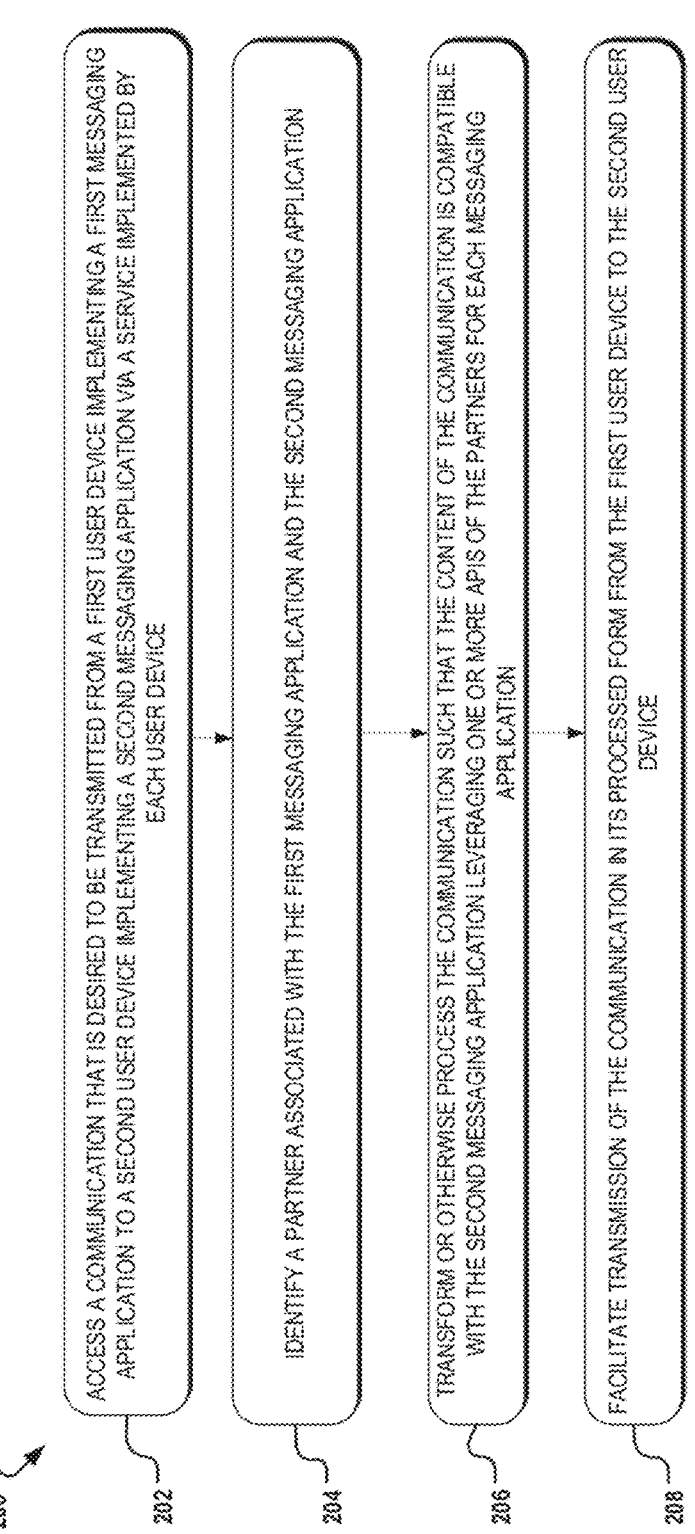
FIG. 2 is an exemplary process flow for universal secure messaging.

Referring now to a process flow diagram 200 of FIG. 2 and with continuing reference to FIGS. 1A-1B, one exemplary implementation of the platform 111 defined by the system 100 shall now be described. It should be understood that the process flow diagram 200 illustrates exemplary functionality of the system 100 such that other features are contemplated, and the steps and functionality shown may be iteratively provided or repeated as needed to essentially form the hub 150 of FIG. 1B. Referring to block 202, the computing device 102 may access a request to transmit a communication between the first user device 114A and the second user device 114B. As indicated above, the communication (117) may include by example a message or contact on-call resource from a medical worker to a physician.

Referring to block 204, the computing device leverages the communications and broker logic 120 to identify the partners associated with each of the messaging application 114A and the messaging application 115B being implemented by the first user device 114A and the second user device 114B, respectively, so that the communication can be effectively transmitted. This step is useful for determining how to securely, accurately, and completely transmit the communication between the first user device 114A and the second user device 114B. For example, in one embodiment, the computing device 102 identifies that the first messaging application 115A being implemented by the first user device 114A is supported by the partner server 130. As such, this step informs the computing device 102 that it should access the messaging data 132 (e.g., utilizing API functions 122) or otherwise access information about the messaging data 132 so that it understands, e.g., the specific protocols of the messaging application 115A.

Referring to block 206, the computing device 102 transforms or otherwise translates content of the communication 117 in some form so that the communication is compatible with the second messaging application 115B, where it can be viewed by the physician despite the physician not utilizing the first messaging application 115A. As indicated herein, API integration with partners such as the partner server 130 may be utilized to achieve this step. For example, the computing device 102 may utilize the API functions 122 to make one or more API calls to the partner server 130 or other devices to 102 transform or otherwise translate content of the communication in some form so that the communication is compatible with the second messaging application 115B and can be viewed by the physician.

Referring to block 208, the communication (e.g., 117) as processed or translated is provided to the second user device 114B via the messaging application 115B. The medical worker and the physician may be oblivious to the present step and the aforementioned steps, with the computing device 102 brokering the communication in the background and delivering the communication 117 despite each of the user devices 114 using different messaging and/or EHR systems.

Other features of the hub 150 and system 100 are contemplated. The service 116 for example may be implemented as a layer of software provided over the messaging applications 115. The hub 150 may function as a traffic router, and by allowing medical workers to continue messaging on preferred applications or platforms, reduces risk of exposure of privacy or sensitive data. In some embodiments, the hub 150 is an enterprise service bus (ESB) that translates messages to a predetermined format or type, and routes messages between different EHR systems or messaging applications.

Figure 3:
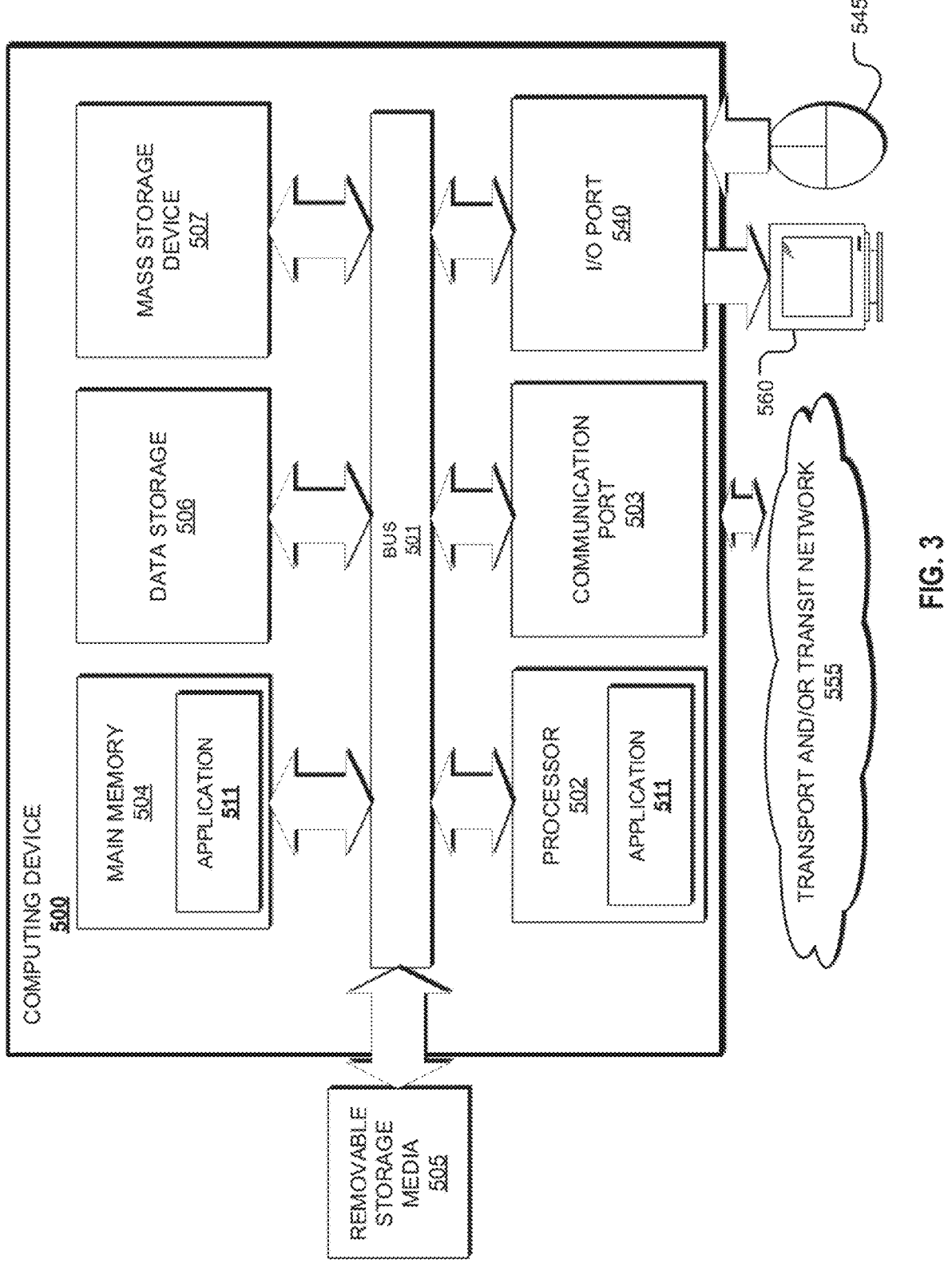
FIG. 3 is a simplified schematic diagram illustrating an exemplary computing device that may be configured to implement various methodologies described herein.

Referring to FIG. 3, a computing device 500 is illustrated which may take the place of the computing device 102 and be configured, via one or more of an application 511 or computer-executable instructions, to execute functionality described herein. More particularly, in some embodiments, aspects of the authentication methods herein may be translated to software or machine-level code, which may be installed to and/or executed by the computing device 500 such that the computing device 500 is configured to execute functionality described herein. It is contemplated that the computing device 500 may include any number of devices, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments, and the like.

The computing device 500 may include various hardware components, such as a processor 502, a main memory 504 (e.g., a system memory), and a system bus 501 that couples various components of the computing device 500 to the processor 502. The system bus 501 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computing device 500 may further include a variety of memory devices and computer-readable media 507 that includes removable/non-removable media and volatile/nonvolatile media and/or tangible media, but excludes transitory propagated signals. Computer-readable media 507 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computing device 500. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, radio frequency (RF), infrared, and/or other wireless media, or some combination thereof. Computer-readable media may be embodied as a computer program product, such as software stored on computer storage media.

The main memory 504 includes computer storage media in the form of volatile/nonvolatile memory such as read only memory (ROM) and random access memory (RAM). A basic input/output system (BIOS), containing the basic routines that help to transfer information between elements within the computing device 500 (e.g., during start-up) is typically stored in ROM. RAM typically contains data and/or program modules that are immediately accessible to and/or presently being operated on by processor 502. Further, data storage 506 in the form of Read-Only Memory (ROM) or otherwise may store an operating system, application programs, and other program modules and program data.

The data storage 506 may also include other removable/non-removable, volatile/nonvolatile computer storage media. For example, the data storage 506 may be: a hard disk drive that reads from or writes to non-removable, nonvolatile magnetic media; a magnetic disk drive that reads from or writes to a removable, nonvolatile magnetic disk; a solid state drive; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules, and other data for the computing device 500.

A user may enter commands and information through a user interface 540 (displayed via a monitor 560) by engaging input devices 545 such as a tablet, electronic digitizer, a microphone, keyboard, and/or pointing device, commonly referred to as mouse, trackball or touch pad. Other input devices 545 may include a joystick, game pad, satellite dish, scanner, or the like. Additionally, voice inputs, gesture inputs (e.g., via hands or fingers), or other natural user input methods may also be used with the appropriate input devices, such as a microphone, camera, tablet, touch pad, glove, or other sensor. These and other input devices 545 are in operative connection to the processor 502 and may be coupled to the system bus 501, but may be connected by other interface and bus structures, such as a parallel port, game port or a universal serial bus (USB). A monitor 560 or other type of display device may also be connected to the system bus 501. The monitor 560 may also be integrated with a touch-screen panel or the like.

The computing device 500 may be implemented in a networked or cloud-computing environment using logical connections of a network interface 503 to one or more remote devices, such as a remote computer. The remote computer may be a personal computer, a server, a router, a network PC, a peer device or other common network node, and typically includes many or all of the elements described above relative to the computing device 500. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computing device 500 may be connected to a public and/or private network through the network interface 503. In such embodiments, a modem or other means for establishing communications over the network is connected to the system bus 501 via the network interface 503 or other appropriate mechanism. A wireless networking component including an interface and antenna may be coupled through a suitable device such as an access point or peer computer to a network. In a networked environment, program modules depicted relative to the computing device 500, or portions thereof, may be stored in the remote memory storage device.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a stand-alone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hard-wired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure the processor 502, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

Computing systems or devices referenced herein may include desktop computers, laptops, tablets e-readers, personal digital assistants, smartphones, gaming devices, servers, and the like. The computing devices may access computer-readable media that include computer-readable storage media and data transmission media. In some embodiments, the computer-readable storage media are tangible storage devices that do not include a transitory propagating signal. Examples include memory such as primary memory, cache memory, and secondary memory (e.g., DVD) and other storage devices. The computer-readable storage media may have instructions recorded on them or may be encoded with computer-executable instructions or logic that implements aspects of the functionality described herein. The data transmission media may be used for transmitting data via transitory, propagating signals or carrier waves (e.g., electromagnetism) via a wired or wireless connection.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for universal secure messaging in a healthcare environment, comprising:
  a processor configured to execute one or more processes; and
  a memory storing a process executable by the processor, the process when executed, being operable to:
    access a communication from a first computing device associated with a hospital facility and executing a first universal secure messaging application approved by the hospital facility and used by inpatient clinical staff,
    provide the communication as input to a messaging hub, the messaging hub configured to securely broker communications between different communications platforms including a plurality of vendor-specific secure messaging and on-call management platforms used by external medical providers,
    execute broker logic associated with the messaging hub to identify, based on provider-identifying information included with the communication and on-call scheduling data, a preferred secure messaging platform associated with a target medical provider, and to prepare the communication for transmission to a second computing device, and
    facilitate transfer of the communication from the first computing device to the second computing device associated with the target medical provider, the second computing device executing a second application different from the first application while the first computing device continues to utilize only the first universal secure messaging application, the second application comprising a secure messaging or on-call management application and being native to the preferred secure messaging platform.

2. The system of claim 1, wherein the processor:
  accesses a request to input the communication to the messaging hub from the second computing device.

3. The system of claim 1, wherein the communication includes a message from a first medical worker to a second medical worker associated with a healthcare provider.

4. The system of claim 1, wherein the broker logic includes steps for determining what platform corresponds to the first computing device and the second computing device.

5. The system of claim 1, wherein the processor by execution of the broker logic transforms the communication such that it is compatible with the second application associated with the second computing device.

6. The system of claim 1, wherein the broker logic includes calling one or more application programming interface (API) to determine messaging protocols associated with the second application associated with the second computing device.

7. The system of claim 1, wherein the messaging hub is vendor agnostic.

8. The system of claim 1, wherein the messaging hub is implemented using cloud-based infrastructure configured for secure communications between the first computing device and the second computing device.

9. The system of claim 1, further comprising a universal web application configured to integrate the first application with the second application.

10. The system of claim 1, wherein the messaging broker is implemented as a layer of software provided over the first application and the second application.

11. The system of claim 1, wherein the messaging hub is an enterprise service bus (ESB) that translates messages to a predetermined format or type, and routes messages between different electronic health record EHR systems or messaging applications.

12. The system of claim 1, wherein the messaging hub provides secure bi-directional communications with other secure message applications.

13. The system of claim 1, wherein the messaging hub leverages Application Program Interfaces (APIs) to integrate with known software vendors in the secure messaging and on-call space.

14. A non-transitory, computer-readable medium storing instructions encoded thereon, the instructions, when executed by one or more processors, cause the one or more processors to perform operations to:
  access a communication from a first computing device executing a first application, the communication including clinical information for coordinating patient care,
  provide the communication as input to a messaging hub, the messaging hub configured to securely broker communications between different communications platforms in a healthcare environment,
  execute broker logic associated with the messaging hub to prepare the communication for transmission to a second computing device, wherein executing the broker logic comprises determining what communications platform corresponds to the second computing device and calling one or more application programming interfaces (APIs) to determine messaging protocols associated with the second application, and
  facilitate transfer of the communication from the first computing device to the second computing device executing a second application different from the first application, including transforming the communication such that the communication is compatible with the second application.

15. A method, comprising:
  accessing, by a processor, a communication associated with a first user device related to patient care, the communication initiated from a first messaging application executed by the first user device, the communication intended for a second user device implementing a second messaging application;

accessing, by the processor, messaging data associated with the second messaging application, including by identifying a server supporting the second messaging application and calling one or more application programming interfaces (APIs) associated with the second messaging application to determine messaging protocols of the second messaging application; and transforming or otherwise translating content of the communication for interpretation by the second messaging application such that the transformed communication is compatible with the second messaging application.

\* \* \* \* \*